(12) United States Patent
Ren et al.

(10) Patent No.: US 9,757,282 B2
(45) Date of Patent: Sep. 12, 2017

(54) MEDICAL TOWEL AND METHOD FOR MANUFACTURING

(75) Inventors: XingQuan (Peter) Ren, Chicago, IL (US); Jim O'Brian, Libertyville, IL (US); Tom Pistella, Libertyville, IL (US)

(73) Assignee: Medline Industries, Inc., Mundelein, IL (US)

(*) Notice: Subject to any disclaimer, the term of this patent is extended or adjusted under 35 U.S.C. 154(b) by 814 days.

(21) Appl. No.: 13/197,313

(22) Filed: Aug. 3, 2011

(65) Prior Publication Data

US 2012/0034445 A1 Feb. 9, 2012

Related U.S. Application Data

(60) Provisional application No. 61/370,736, filed on Aug. 4, 2010.

(51) Int. Cl.
*B32B 5/00* (2006.01)
*A61F 13/36* (2006.01)
*A61B 46/00* (2016.01)
*A61F 13/00* (2006.01)

(52) U.S. Cl.
CPC ............. *A61F 13/36* (2013.01); *A61B 46/40* (2016.02); *A61F 2013/00348* (2013.01); *Y10T 428/249921* (2015.04)

(58) Field of Classification Search
USPC ...................... 428/221; 8/139, 107, 111; 26/7
See application file for complete search history.

(56) References Cited

U.S. PATENT DOCUMENTS

| | | |
|---|---|---|
| 6,055,711 A | 5/2000 | Weil et al. |
| 2009/0235498 A1 | 9/2009 | Sun |
| 2009/0270824 A1 | 10/2009 | Kapik et al. |

FOREIGN PATENT DOCUMENTS

| | | |
|---|---|---|
| CN | 1 070 329 A | 3/1993 |
| EP | 0 517 687 A1 | 12/1992 |
| EP | 0 554 049 A1 | 8/1993 |
| WO | WO 2012/018902 | 2/2012 |

OTHER PUBLICATIONS

International Search Report and Written Opinion for International Application No. PCT/US2011/046405, mailed Jan. 18, 2012.
Patent Examination Report No. 1 for Australian Patent Application No. 2011285775, dated Feb. 5, 2014.
Official Action for Chinese Application No. 201180045994.3, dated Mar. 31, 2015.
Official Action for Chinese Application No. 201180045994.3, dated Jan. 18, 2016.
Official Action for European Application No. 11746086.5, dated Dec. 9, 2013.
Extended European Search Report for European Application No. 14171671.2, dated Aug. 12, 2014.
Official Action for European Application No. 14171671.2, dated Jun. 19, 2015.
International Preliminary Report on Patentability for International Application No. PCT/US2011/046405, dated Feb. 5, 2013.
Database WPI, Week 199405, Thomson Scientific, London, GB, AN 1994-035577, 1 page (1994).

*Primary Examiner* — Vincent A Tatesure
(74) *Attorney, Agent, or Firm* — Cooley LLP

(57) ABSTRACT

A dye free medical towel and a method of making thereof, comprising natural, dye free, cotton absorbent cloth material, the towel having a first reduced glare characteristic and reduced linting.

11 Claims, 7 Drawing Sheets

ILL 1 D65-10
ILL 2 F02-10 (CWF)
ILL 3 F02-10 (CWF)

P/F Limit 1.50
Margin 10.00
l:c Ratio 2.00

| Standard Name: | WI-CIE | h° | Date/Time |
| --- | --- | --- | --- |
| OR Towel Sample 1 6-17-2010 | 12.22 | 78.26 | |
| | | 83.59 | |

| Trial Name | WI-CIE | DH*cmc | DEcmc | WI-Berg | P/F DEcmc |
| --- | --- | --- | --- | --- | --- |
| OR Towel Sample 3 6-17-2010 F02-10 (CWF) | 10.94 | 0.14 | 0.20 | 22.61 | Passed |
| | | 0.08 | 0.16 | | |
| OR Towel Sample 2 6-17-2010 F02-10 (CWF) | 7.23 | 0.06 | 0.61 | 20.55 | Passed |
| | | 0.03 | 0.61 | | |

MEDICAL TOWEL AND METHOD FOR MANUFACTURING

RELATED APPLICATION

This application claims priority to U.S. Provisional Application No. 61/370,736 filed Aug. 4, 2010 and entitled "MEDICAL TOWEL," the contents of which are herein incorporated by reference in its entirety.

BACKGROUND

Some embodiments relate generally to absorbent medical products and more particularly to absorbent medical towels for use in healthcare.

Absorbents medical products are prevalent in many aspects of healthcare for use in medical procedures to wound dressings to general cleaning. Medical towels, for example, are used to soak up and absorb bodily fluids such as blood or other exudates resulting from wounds or surgically created openings within the body.

Originally these towels were made of woven cotton and bleached, generally resulting in a bright white towel. The bright white color however produces glare, particularly from operating room lighting causing poor and distracting visual conditions during procedures. The glare is problematic as it results in visual discomfort, and leads to fatigue of operating room staff during surgical procedures. In some cases, it has been observed that the greatest discomfort glare and brightness was at 480 nm and 650 nm. One solution has been to add dye coloring to the absorbent material in an attempt to reduce the glare. However this results in additional steps to manufacture the product and further reduces the absorbency of the towel.

In many instances, the dyeing portion of the process is subcontracted to an outside dye-house, which process medical towels under the same production line as other non-medical products i.e. garment, fabric etc. Fabric is handled in an open production line separated into steps including degreasing, dyeing, bleaching and washing etc. Additionally, bleaching further increases linting due to the mechanical breakdown from the bleaching process, particularly with chlorine based bleaches.

This open production line separated into steps involves in extensive handling and chemical treatment on fabric in a non-controlled environment, which reduces the hygiene level and absorbency of the fabric, as well as increasing the lint. Lint is a well known cause of infection and if introduced into a body cavity, it can have serious life threatening implications. All surgical products introduced to the sterile field or close to the surgical site are generally required to have no or low linting characteristics.

The 2009 new prospective payment plan from CMS (Centers for Medicare and Medicaid Services) are requiring hospitals to be financially accountable for Surgical Site Infections (SSI). Therefore an increased awareness that "causes of surgical site infections" can be prevented is heightened more then ever before. In the United States it's reported that between 500,000 and 750,000 SSIs occur annually and the median costs of a surgical site infection is approx. $62,908 per patient according to Engemann J J, Carmeli Y, Cosgrove S E, et al. http://www.infectioncontroltoday.com/articles/reducing-surgical-infections.html
The CDC (Centers for Disease Control) has revised their guidelines for prevention of SSI for facilities to implement these guidelines (http://www.cdc.gov/ncidod/eid/vol7no2/nichols.htm) and to reduce lint in accordance with these guidelines.

In order to reach the surgical standard, the fabric has to be reprocessed including washing and drying afterwards in a controlled environment.

Thus, there is a need for an eco-friendly, reduced glare, low lint, dye-free, absorbable towel for medical use.

BRIEF DESCRIPTION OF THE DRAWINGS

FIG. 6 is a table showing whiteness index measurements for a first medical towel sample and a second medical towel sample.

DETAILED DESCRIPTION

Figure 1:
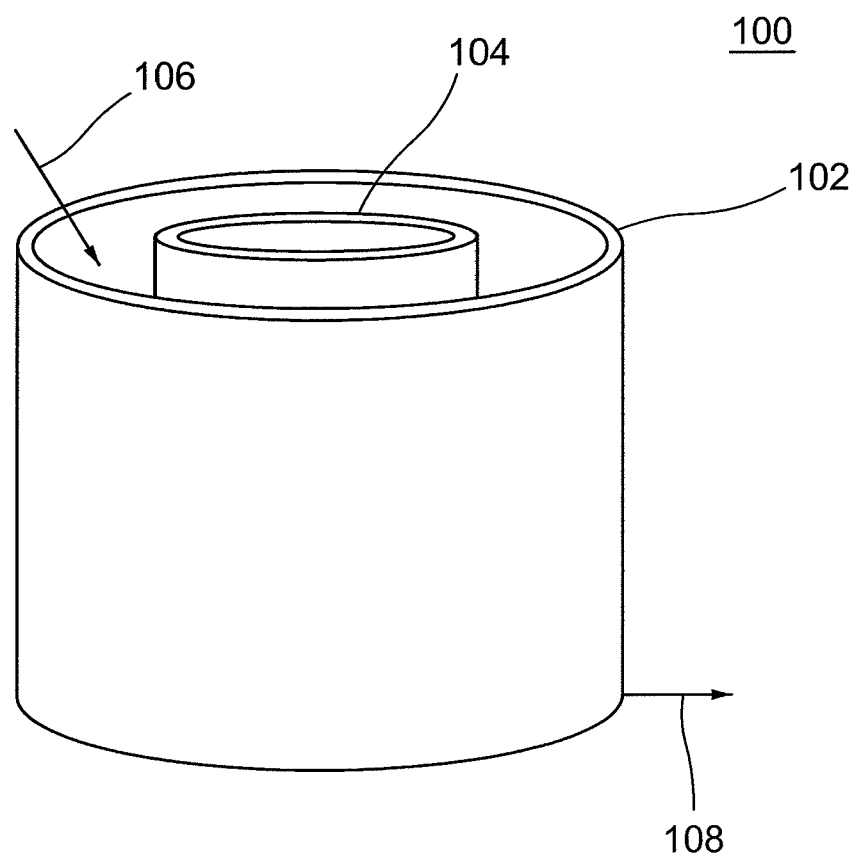
FIG. 1 is a processing tank for the dye free medical towel

In describing the embodiments of the invention in detail and referring to the drawings, like numbers indicate like parts throughout the figures. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

Embodiments of the invention provide a natural fiber medical towel ("natural towel" or "medical towel") that has reduced lint, increased absorbency and low glare characteristics. In so doing, embodiments of the invention work to provide a dye-free natural cloth with increased absorbency concurrently with reduced reflectivity and further reduced amounts of lint. This leads to an environmentally friendly towel that has acceptable lint levels for medical procedures such as those in the sterile environment of the operating room. As used in this description, "natural towel," "natural fiber" and similar terms indicate materials that have the characteristics of the novel medical towel and method of manufacture described herein. Such terms should not be understood to include or imply any additional limitation beyond those expressly described.

In one embodiment, the medical towel is comprised of natural cotton, dye free absorbent cloth material, the medical towel having a first reduced glare characteristic. Glare can be based on visual observations under operating room conditions as well as measured percent reflectance and/or transmittance of light at a given wavelength or frequency band. Additionally, the whiteness (WI) of the fabric can have an effect on the reflectivity and glare of the medical towel. The medical towel can have increased fluid retention characteristics over absorbent towels of the past as well as reduced glare, without the need for the application of glare reducing agents such as dyes, films or the like.

In one embodiment, the medical towel can be used in an operating room (OR) during surgical procedures. The medical towel may be sterilized and may be used intra-operatively as a surgical drape barrier, reinforcement for table covers, rolls for instruments, and/or as for intra-cavity packing for open patient procedures, such as, for example, open-heart or open abdominal. The medical towel can be less linty, more absorbent, hypo-allergenic and more environmentally friendly than traditionally dyed OR towels.

In one embodiment, advantages of the medical towel can include environmentally friendly processing resulting in an environmental friendly product. White, bleached OR towels and drapes used in the past, migrated toward a darker colors (e.g. green & blue), and moved away from the solid white color, due to glare issues from the intense surgical lighting. In this embodiment, the medical towel fibers are processed so as to retain the natural color of the cotton and can result in glare characteristics that are surprisingly favorable under OR lighting conditions. In this embodiment, the natural color can be substantially similar to a pantone matching system number 400. Removing the entire dye process, which is typically done by a third party supplier, further removes the chlorine bleaching process that occurs as a preparation step for the addition of the dye to the fabric. The elimination of the chlorine bleach step can further reduce the amount of lint and other contaminants introduces as a result of the extra steps.

In this embodiment the process of treating the medical towel can substantially eliminate the bleaching, can completely eliminate the dyeing process, can consolidate the degreasing and washing into one step under high-temperature/high-pressure and can include a triple-wash procedure. The medical towel fibers can have minimal exposure to high chemical dyeing/bleaching material/process and eliminate pollution resulting from the presence of the dye. Some dyes may cause harm to the tissue or organs coming in contact with as well as post-op healing complications, particularly if not properly bonded to the fabric. Washing in a high-temperature/high-pressure & triple-wash procedure can improve the cleanliness of products and enable the fabric to maintain the hygiene level while substantially preserving the natural color.

Another object of the present invention is to provide a method for producing a medical towel with color and reflectance characteristics that reduce the glare and reflectivity associated with a solid white color. By consolidating the degreasing and washing into one step, and eliminating bleaching and dyeing, the manufacturing process steps of the medical towel can result in better color control thereby substantially maintaining the natural color of medical towel fibers at a predetermined level that can reduce the glare and reflectivity.

Still another objective of the present invention is to provide a medical towel with absorbent and low lint characteristics. By using this "one-step" manufacturing process (i.e. elimination of the dyeing process), the medical towel fibers are maintained in a controlled system without extensive exposure or handling of the medical towel fibers, resulting in reduced lint levels. Further, the triple wash procedure can remove exiguous impurities including cotton knots, can improve the cleanness of products, and can result in a medical towel that meets or exceeds the absorbency of current OR towels. The standards for laboratory tests demonstrate surprisingly favorable result for wicking rate, absorbent capacity, and Gelbo-flex linting.

In one embodiment the medical towel, can include a plurality of woven cotton fibers that are natural and dye-free, and has a reflectance percentage that can be below about 75 percent, measured at all wavelengths between about 360 nm and about 750 nm. Woven cotton fibers are implemented as one embodiment, it is understood however that the medical towel may be embodied in other forms including but not limited to non-woven forms as well. In another embodiment, the percent reflectance can be about 60 percent or less at wavelengths at or below about 600 nm and can be greater than about 25 percent at wavelengths between about 360 nm and about 750 nm. In one embodiment, the percent reflectance can be less than about 75 percent and can be greater than about 25 percent, and the Whiteness can be less than about 20 percent WI. In one embodiment the color of the natural towel can be substantially equivalent to 400 of the pantone matching system (PMS). In yet another embodiment, the percent reflectance can be less than about 50% at a wavelength of about 480 nm. In this embodiment, the percent reflectance can be greater than about 25 percent at a wavelength of about 360 nm.

In one embodiment the natural color of the cotton fibers used in combination with the processing characteristics can result in a medical towel with a natural color substantially similar or equivalent to 400 PMS, and can have a whiteness index less than 75% WI-CIE, measured in accordance with ASTM Test Method E313-05, D65-10 as the illumination source standard. ASTM Test Method E313-05 generally, is the method used in the standard practice for calculating yellowness and whiteness indices from instrumentally measured color coordinates in measuring the whiteness of the medical towels. Whiteness index (WI) is the degree to which a surface is white. D65-10 is only one exemplary standard illuminant and it is realized by those of ordinary skill in the at that other illumination conditions may be used however, every operating room is different and lighting equipment and range of color temperature differ as well and hence the D56-10 standard illuminant was chosen as the standard of measure. Other standards include, the Ganz-Griesser Whiteness Index, the European standard BS EN 14079:2003, Chinese standard YY0330-2002, Medical Purified Cotton Standard. For clarity, the ASTM Test Method E313-05 will be used unless another standard is specifically referenced.

Towels with a whiteness less than about 75% WI-CIE can exhibit reduced luminescence and reduced reflected (specular) glare and therefore can exhibit favorable characteristics for use in medical procedures under operating room lighting conditions. In one embodiment the whiteness can be less than about 50% WI-CIE. In still another embodiment the whiteness can be less than about 30% WI-CIE and can be between about 7% and about 17% WI-CIE as per ASTM Test Method E313-05, D65-10 standard illuminant. In one embodiment, the towel can have a whiteness between about 7% and about 17%, can have a percent reflectance of less than about 50% at wavelengths below about 500 nm, and can have a natural color yellow measured at about 10%, giving the towel low glare. This further can retain the natural fiber characteristic look. Because the towel is dye-free, the natural color, which can appear as a tan in this embodiment, is achieved by the natural color of the cotton used in conjunction with the process of forming the towel. In one embodiment, removing the bleaching process, which is typically used in the dyeing stage of the manufacturing process, prevents the unwanted whitening, of the cotton fibers of the medical towel. In one embodiment, removal of chlorine bleach of the dye stage can prevent the whitening of the fibers. Further the three stage, or triple wash, can rinse the medical towel fibers at multiple temperatures sufficiently to clean the cloth while preserving the natural color and maintaining a reduced amount of overall lint.

In another embodiment, the towel can have a whiteness between about 7% and about 17%, can have a percent reflectance of less than about 50% at wavelengths below about 500 nm, and can have a natural color yellow of substantially similar to 400 PMS measured at about 10%, and can result in the towel having a low glare.

In one embodiment, $H_2O_2$, a mild bleach, can be used in low concentrations in the degreasing stage, i.e. removal of the wax and other unwanted foreign material on the cotton fibers. In one embodiment about 10% on weight of fiber (o.w.f.) $H_2O_2$ can be used. In another embodiment NaOH at a concentration of about 5% o.w.f. can be used with the 10% o.w.f. $H_2O_2$.

Surprisingly, when chlorine bleach, generally used to prepare the material for the dye process, is removed the amount of lint present can go down. Although it is assumed that the absorbency would increase as a result of the lack of dye, it was not expected that the lack of the opening of the fiber by the chlorine bleach would also lead to an increased absorbency.

Absorbency is measured based on a standard wicking test (AATCC (American Association of Textile Chemists and Colorists) TS017) standard and a standard surface water absorption of Terry Fabric (Water Flow Test)—ASTM D4772. The wicking test demonstrates the speed and rate of fluid spread for a fabric. A 20 mm length test strip and a 30 mm length test strip is submerged in liquid and the speed is measured based on how fast the fluid travels through the fabric. The average fluid travel rate for a natural towel is 2.75 mm/Second, while it is 1.5 mm/Second for a blue dyed towel, equivalent to an 83% increase. The Water Flow Test determines the ability of a terry fabric to rapidly absorb and retain liquid water. In general, in this test, specimens are placed one at a time in an embroidery hoop and then the hoop/specimen assembly is placed at an angle on the base of the apparatus. After water flows down the surface of each specimen, the amount of water retained by each specimen is measured. Six specimens are tested, three on the face of the fabric and three on the back of the fabric. The six observations are averaged to determine the surface water absorption of the fabric. The average absorbency rate for a natural towel is about 3.31 gram of water per 1 gram of fabric, while a blue dyed towel retains less than 1 gram of water per gram of fabric.

Table 1 shows the absorption rate wick test results for one embodiment of the medical towel. In this embodiment, the natural medical towel was processed without the dye stage, and processed with the triple wash procedure and a degreasing stage using NaOH at a concentration of about 5% o.w.f. and about 10% o.w.f. $H_2O_2$. These results show a significant increase in absorbency wicking rate over dyed towels. Table 2 shows the absorption rate wick test results for a dyed towel. This is done in accordance with the standard, AATCC TS017.

TABLE 1

ABSORPTION RATE WICKING TEST-NATURAL WOVEN AATCC TS017

| ORIGINAL WICK | 20 MM | | 30 MM | |
| --- | --- | --- | --- | --- |
| TIME, S | WARP | WEFT | WARP | WEFT |
| 1 | 10 SEC | 10 SEC | 12 SEC | 12 SEC |
| 2 | 7 SEC | 9 SEC | 9 SEC | 11 SEC |
| 3 | 8 SEC | 10 SEC | 10 SEC | 12 SEC |
| 4 | 9 SEC | 8 SEC | 11 SEC | 10 SEC |
| 5 | 8 SEC | 9 SEC | 10 SEC | 11 SEC |
| AVG | 8 SEC | 9 SEC | 10 SEC | 11 SEC |

TABLE 1-continued

ABSORPTION RATE WICKING TEST-NATURAL WOVEN AATCC TS017

| ORIGINAL WICK | 20 MM | | 30 MM | |
| --- | --- | --- | --- | --- |
| TIME, S | WARP | WEFT | WARP | WEFT |
| AVG WICK RATE | | | | |
| FOR 20 MM, MM/S | 3.0 MM/S | 2.0 MM/S | — | — |
| FOR 30 MM, MM/S | — | — | 3.0 MM/S | 3.0 MM/S |

TABLE 2

ABSORPTION RATE WICKING TEST-BLUE WOVEN AATCC TS017

| ORIGINAL WICK | 20 MM | | 30 MM | |
| --- | --- | --- | --- | --- |
| TIME, S | WARP | WEFT | WARP | WEFT |
| 1 | 12 SEC | 15 SEC | 14 SEC | 17 SEC |
| 2 | 14 SEC | 17 SEC | 16 SEC | 19 SEC |
| 3 | 15 SEC | 17 SEC | 17 SEC | 19 SEC |
| 4 | 14 SEC | 15 SEC | 16 SEC | 17 SEC |
| 5 | 17 SEC | 15 SEC | 19 SEC | 17 SEC |
| AVG | 14 SEC | 16 SEC | 16 SEC | 18 SEC |
| AVG WICK RATE | | | | |
| FOR 20 MM, MM/S | 1.0 MM/S | 1.0 MM/S | — | — |
| FOR 30 MM, MM/S | — | — | 2.0 MM/S | 2.0 MM/S |

Table 3 and Table 4 show the surface water absorption of terry fabrics in accordance with ASTM 4772 standard. These tables show that the weight of water per weight of fabric for the natural medical towel was 3.31 while the weight of water per weight of fabric for the dyed towel was about 0.9.

TABLE 3

SURFACE WATER ABBSORPTION OF TERRY FABRICS (WATER FLOW TEST)-ASTM 4772 COLOR: NATURAL WOVEN

| | ABSORBED (ML) | | ABSORBENCY |
| --- | --- | --- | --- |
| | FACE | BACK | (%) |
| 1) | 15.0 | 12.0 | 27.0 |
| 2) | 12.0 | 14.0 | 26.0 |
| 3) | 14.0 | 12.0 | 26.0 |
| AVERAGE: | 13.7 | 12.7 | |
| OVERALL AVERAGE WEIGHT OF WATER ABSORBED (GRAMS) | 13.2 | | 26.3 |
| WEIGHT OF WATER ABSORBED (GRAMS) | 13.2 | | — |
| WEIGHT OF FABRIC, 6 INCH DIAMETER (GRAMS) | 3.990 | | — |
| WEIGHT OF WATER PER WEIGHT OF FABRIC | 3.31 | | — |

TABLE 4

COLOR: BLUE WOVEN

| | ABSORBED (ML) | | ABSORBENCY |
|---|---|---|---|
| | FACE | BACK | (%) |
| 1) | 5.0 | 4.0 | 9.0 |
| 2) | 4.0 | 4.0 | 8.0 |
| 3) | 2.0 | 5.0 | 7.0 |
| AVERAGE: | 3.7 | 3.0 | |
| OVERALL AVERAGE | 3.4 | | — |
| WEIGHT OF WATER ABSORBED (GRAMS) | 3.4 | | — |
| WEIGHT OF FABRIC, 6 INCH DIAMETER (GRAMS) | 3.796 | | — |
| WEIGHT OF WATER PER WEIGHT OF FABRIC | 0.90 | | — |

Table 5 shows the results for linting as a function of particulate size. The standard for measuring the amount of lint is the Gelbo-Flex test. The Gelbo-Flex test counts the amount of dry particulate released from the test sample during a 300 second flex (value doubled for particles released/minute). Particles are counted in size from about 0.5 to about 25 micros. The natural medical towel released about 58089 particles at 0.5 micron and larger.

TABLE 5

| | PARTICULATE SIZE (μm) | | | | | | TOTAL LINTING | |
|---|---|---|---|---|---|---|---|---|
| TOTAL | 0.3 | 0.5 | 1 | 5 | 10 | 25 | ≥0.3 | ≥0.5 |
| BLUE | 263234 | 351905 | 353842 | 15255 | 1546 | 878 | 987259 | 723715 |
| NATRUAL | 17963 | 25711 | 29436 | 1904 | 571 | 480 | 76057 | 58089 |
| RATE | 14 | 12 | 8 | 3 | 2 | 13 | 12 | 12 |

TABLE 6

GELBO FLEX TEST
AVERAGE OF TEST PIECES 1-5
Side A: Natural B

| | Particulate Size (μm) | | | | | | TOTAL LINTING | |
|---|---|---|---|---|---|---|---|---|
| Period (sec.) | 0.3 | 0.5 | 1.0 | 5.0 | 10.0 | 25.0 | ≥0.3 | ≥0.5 |
| 30 | 4502 | 7209 | 10303 | 925 | 307 | 332 | 23578 | 19077 |
| 60 | 3369 | 5343 | 6795 | 471 | 139 | 90 | 16207 | 12838 |
| 90 | 2449 | 3551 | 4050 | 246 | 62 | 45 | 10404 | 7955 |
| 120 | 1882 | 2747 | 2940 | 163 | 41 | 26 | 7799 | 5917 |
| 150 | 1704 | 2347 | 2306 | 104 | 18 | 19 | 6498 | 4795 |
| 180 | 1532 | 2049 | 1952 | 81 | 16 | 14 | 5645 | 4113 |
| 210 | 1491 | 1948 | 1878 | 78 | 19 | 15 | 5429 | 3939 |
| 240 | 1477 | 1850 | 1656 | 56 | 12 | 9 | 5060 | 3583 |
| 270 | 1439 | 1760 | 1560 | 59 | 13 | 10 | 4841 | 3401 |
| 300 | 1456 | 1773 | 1651 | 74 | 15 | 10 | 4979 | 3523 |
| | | | | | | | | |
| Total | 21301 | 30577 | 35092 | 2256 | 644 | 571 | 90441 | 69140 |
| Total - C0 | 21282 | 30568 | 35083 | 2255 | 643 | 571 | 90402 | 69120 |
| Std Dev | 11023 | 14646 | 15257 | 797 | 187 | 237 | 41766 | 30842 |
| Coef of Var | 52 | 48 | 43 | 35 | 29 | 41 | 46 | 45 |
| Coef of Linting: | | | | | | | 4.96 | 4.84 |

TABLE 7

AVERAGE OF TEST PIECES 6-10
Side B: Natural B

| | Particulate Size (μm) | | | | | | TOTAL LINTING | |
|---|---|---|---|---|---|---|---|---|
| Period (sec.) | 0.3 | 0.5 | 1.0 | 5.0 | 10.0 | 25.0 | ≥0.3 | ≥0.5 |
| 30 | 2851 | 4614 | 6687 | 632 | 241 | 215 | 15239 | 12388 |
| 60 | 2254 | 3517 | 4501 | 329 | 91 | 59 | 10751 | 8497 |
| 90 | 1631 | 2451 | 2738 | 152 | 42 | 24 | 7038 | 5406 |
| 120 | 1284 | 1835 | 1963 | 116 | 31 | 24 | 5253 | 3969 |
| 150 | 1214 | 1640 | 1656 | 78 | 21 | 15 | 4625 | 3411 |

TABLE 7-continued

AVERAGE OF TEST PIECES 6-10
Side B: Natural B

| Period (sec.) | Particulate Size (μm) | | | | | | TOTAL LINTING | |
| --- | --- | --- | --- | --- | --- | --- | --- | --- |
| | 0.3 | 0.5 | 1.0 | 5.0 | 10.0 | 25.0 | ≥0.3 | ≥0.5 |
| 180 | 1138 | 1492 | 1423 | 58 | 19 | 14 | 4144 | 3006 |
| 210 | 1096 | 1402 | 1282 | 52 | 13 | 9 | 3854 | 2758 |
| 240 | 1097 | 1334 | 1239 | 42 | 11 | 8 | 3732 | 2634 |
| 270 | 1035 | 1296 | 1177 | 46 | 11 | 8 | 3574 | 2539 |
| 300 | 1039 | 1273 | 1115 | 47 | 17 | 13 | 3503 | 2464 |
| Total | 14641 | 20853 | 23780 | 1552 | 497 | 389 | 61712 | 47071 |
| Total - C0 | 14625 | 20847 | 23778 | 1547 | 496 | 388 | 61682 | 47057 |
| Std Dev | 6988 | 9137 | 9026 | 392 | 131 | 102 | 25642 | 18711 |
| Coef of Var | 48 | 44 | 38 | 25 | 26 | 26 | 42 | 40 |
| Coef of Linting: | | | | | | | 4.79 | 4.67 |

Skin irritation test results show that the towels are non-irritating in accordance with the ISO 10993-10: 2002 test standard. The test was designed to determine the dermal irritation potential of the test article on the shaved skin of the rabbit as required by regulation of medical device biocompatibility. In one embodiment, 6 patches of approximately 1×1 inches cut from towel sample were wet with tap water and applied to the shaved skin of three adult albino rabbits. After a minimum four hours exposure period, the patches were removed. Observation for skin irritation were conducted after unwrapped. Based on the Primary Irritation Score result, the results indicate that the natural medical towel has the lowest possible score of zero tested at 60 minutes, twenty four hours, forty eight hours and seventy two hours according to the standard. Therefore, the towels are considered a non-irritant.

FIG. 1 illustrates a processing system 100 as one embodiment for producing a medical towel. In this embodiment, a processing tank 102 has an in-let 104 and an outlet 106. A bulk roll 108 ("fabric 108") of materials, e.g., natural fibers, can be placed in the processing tank 102. While described as a bulk roll, materials for the medical towel can be placed in the processing tank 102 in other configurations, such as, for example, pre-cut to an intermediate size, pre-cut to a final size, loose, and/or combinations of sizes and configurations. The size and shape of the bulk roll is not shown to scale and is by way of example only, as will be understood by those of ordinary skill in the art. The process of producing the natural medical towel is carried out in a condensed system/chamber generally called a—High-temperature/High-pressure Degreasing & Triple-Washing System. This process eliminates dyeing and bleaching steps and, as a result, the fabric 108 can be exposed to less chemicals, and ultimately can result in the medical towel having reduced lint and reduced glare and in general, can be a more natural, environmentally friendly medical towel without the dye and the use fewer chemical in the processing stages. Consolidating the degreasing step and the washing step can result in a medical towel that can be more hypo-allergenic and more absorbent than a towel produced using other processes. Furthermore, eliminating the dyeing and bleaching process, can reduce the amount of resources used in producing the medical towel.

Figures 2, 3:
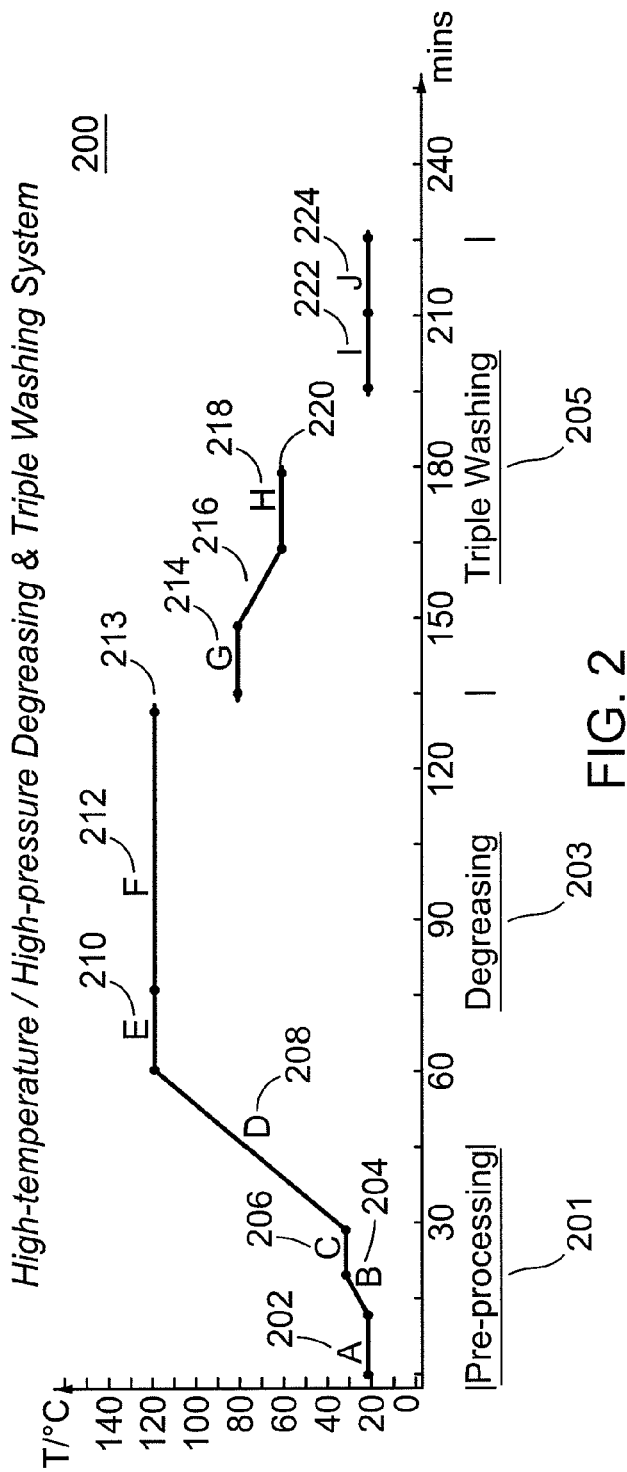
FIG. 2 is an exemplary process chart for a dye free medical towel.
FIG. 3 is a table showing whiteness index measurements.

FIG. 2 illustrates, in chart form, one example of the processing steps for processing the fabric 108 for creating a medical towel. The process is broken down into three phases: the pre-processing phase 201, the degreasing phase 203, and the triple washing phase 205. These phases are all carried out in the batch processing system 100 of FIG. 1. In this embodiment, the fabric 108 may not be removed during the process, for example, for the addition of chlorine bleach or dye, or any other treatments. In the preprocessing phase water can be added to the tank 102 at a temperature of about 20 degrees Celsius (° C.), and the pressure can be increased (at 202). In one embodiment, the pressure can be about 3 Kg per cm². It is understood by those of ordinary skill in the art that the pressure may be chosen in accordance with general towel preprocessing and scouring steps.

A scouring agent can be added to the tank (at 204). The scouring agent in one embodiment can be a mixture of alcohol ethoxylate and Sodium Alkyl Sulfonate (SAS). In this embodiment the scouring agent can be about 1.5% o.w.f ethoxylate and SAS. The Pressure in the degreasing stage can be preferably about 3 Kg/cm² and the pressure in the triple washing stage can be about 2 Kg/cm². After the pressure is increased, the fabric 108 can be allowed to soak (at 206). In one embodiment the soak period can be about five minutes.

Next, the fabric 108 can be degreased (at 203). Degreasing can remove unwanted impurities such as wax and other particulates on the cotton fibers of the fabric. In this stage, the process can include, heating the solution temperature to about 120° C. (at 208). In this embodiment, the temperature can gradually increased over a one hour time period to about 120° C. Once at about 120° C., NaOH at about 5% o.w.f and $H_2O_2$ at about 10% o.w.f can be added (at 210). In this embodiment the time to add these can be about ten minutes. Then the fabric 108 can be allowed to soak for about 80 minutes in one embodiment (at 212). The mixture can then be drained from the tank.

Continuing with FIG. 2, after the degreasing phase 203, the fabric 108 can be washed (which can also be referred to a rinsing) in a three stage rinse phase 205. First, rinse water can be added to the tank at a temperature of 80° C., for the first rinse stage (at 213). The pressure in this embodiment in the tank for this phase can be about 2 Kg/cm². In one embodiment, the fabric 108 can be agitated or the water can be agitated within the tank 102, while in other embodiments, the material can be static within the tank 102. In one embodiment, the fabric 108 can be washed for about 15 minutes (at 214) and then the temperature of the water can be reduced to about 60° C. (at 216). For the second wash stage of the triple rinse phase, the fabric 108 can be washed at about 60° C. for about 15 minutes (at 218). After the second washing stage, the water can be drained from the tank (at 220).

The third washing stage, can begin with adding water at about 20° C. (at 222). The material is washed for about 15 minutes in this stage (at 222). After about 15 minutes, the pH of the mixture can be adjusted to about neutral (at 224). After the adjustment, the water can be removed from the tank 102 and the fabric 108 can be dried and then cut and prepared into towels of desired size. In one embodiment the towel size is about 17 inches by about 25 inches, plus or minus about 2 inches and in rectangular form. In this embodiment, the weight of the towel can be about 60 grams plus or minus about 10 grams and preferably plus or minus about 5 grams.

An overall degreasing process time can be ninety minutes, surprisingly can result in lower reflectivity, whiteness and glare of the finished medical towel. The degreasing period at a first temperature of about 120° C. for about 90 minutes can result in a reflectance of less than about 75 percent and greater than about 25 percent measured over a wavelength between about 360 nm to about 750 nm. In this embodiment the degreasing solution can contain NaOH at 5% o.w.f and $H_2O_2$ at 10% o.w.f.

In one embodiment, all three phases can occur as a batch process. In other words, the fabric 108, can be processed in the same tank from the first phase to the third phase. The fabric 108 can be removed from the tank for drying and then packaging. This process can be take place in a single tank as opposed to a multiple tanks, because there is no need to remove the towel roll from the initial processing (degreasing, triple washing) and transfer it to another tank for bleaching and dyeing.

Figure 4:
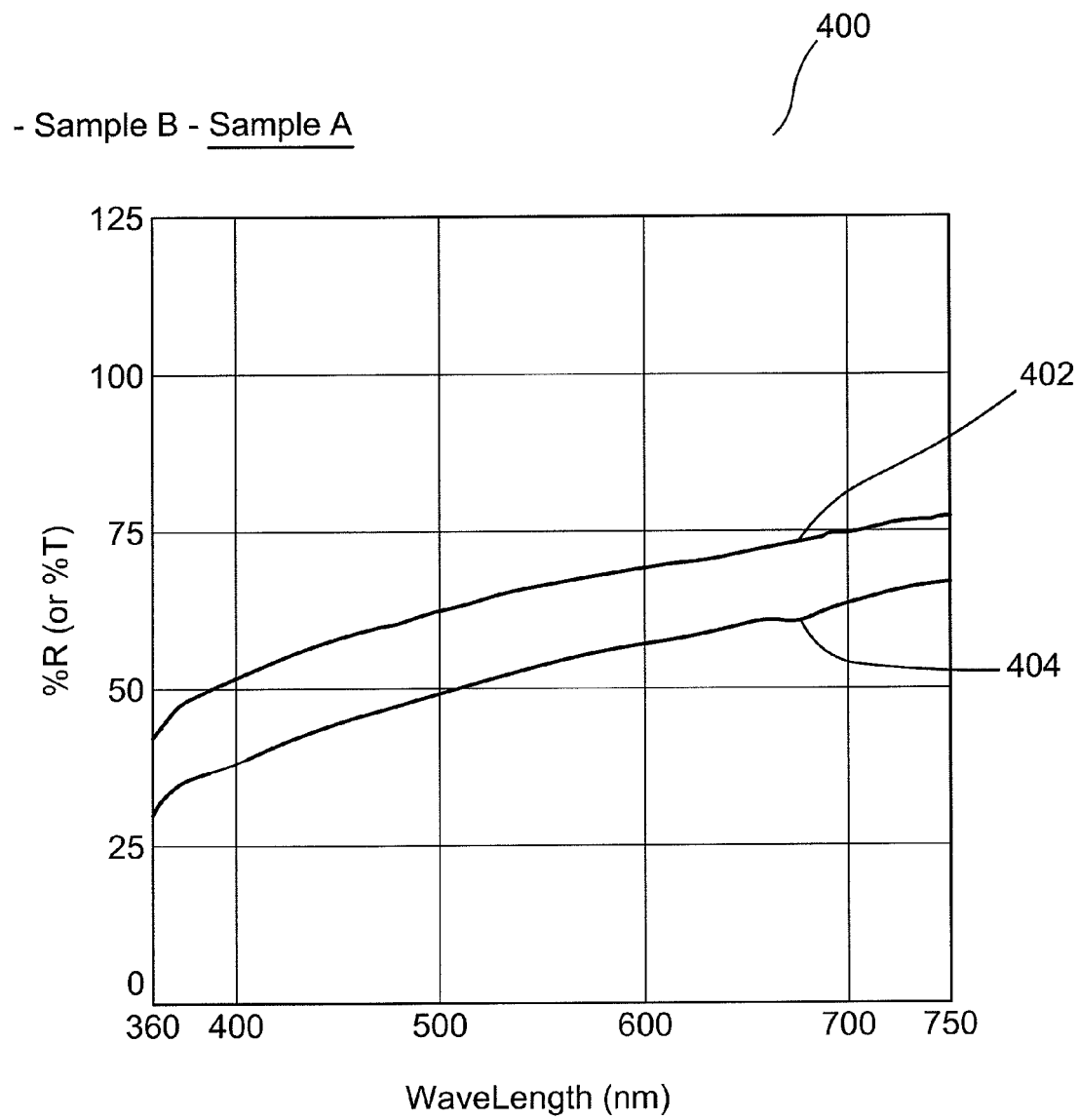
FIG. 4 is an exemplary graphical illustration of the reflectivity for a first and second sample towel as a function of wavelength.
Figure 5:
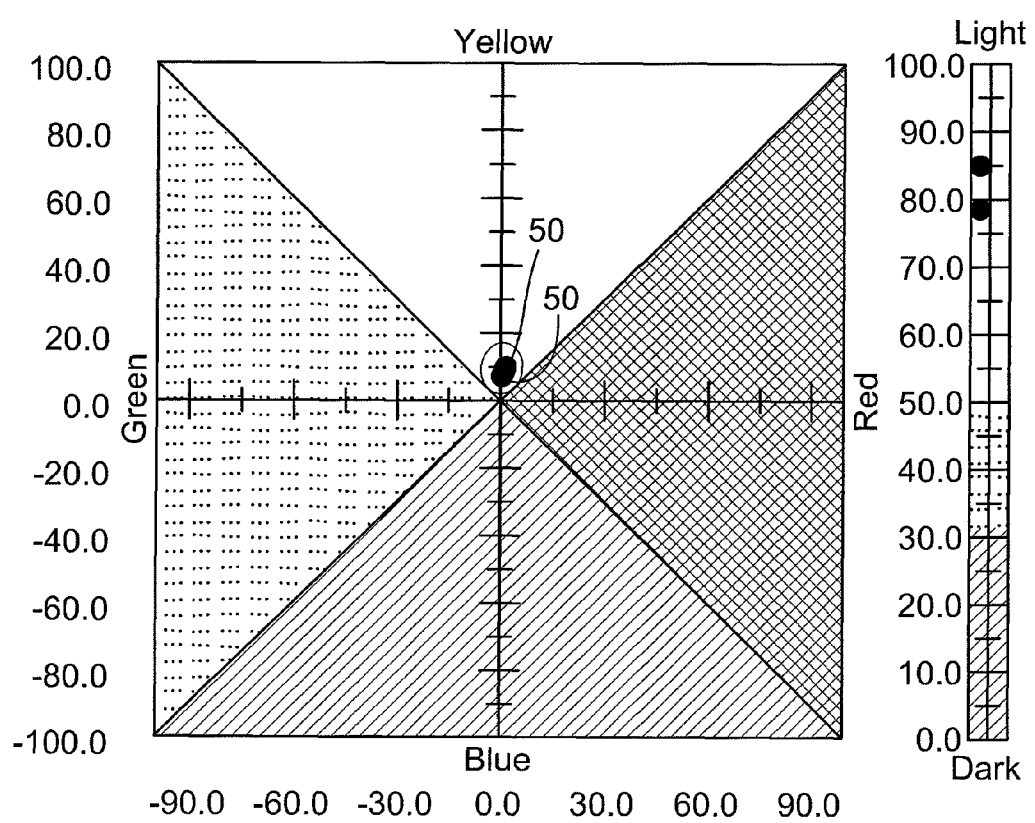
FIG. 5 is a color chart for the first and second samples.

In a first embodiment, the whiteness, reflectance and color characteristics of the natural towel can be illustrated in FIGS. 3-5. FIG. 3 illustrates the whiteness of two samples, whiteness measurements in WI-CIE and in WI-Berg. FIG. 4 illustrates the percent reflectance as a function of the wavelength of light. FIG. 5 illustrates the color. In this embodiment, the whiteness of sample A can be about 30.41 WI-CIE and the percent reflectance (FIG. 4) can be greater than about 50 percent at 400 nm and less than or equal to about 75 Percent at 700 nm. The color (FIG. 5) can be measured along the yellow axis at about 10%.

The whiteness of sample B can be about 3.22 WI-CIE and the percent reflectance can be greater than about 25 percent at 400 nm and less than or equal to about 65 percent at 700 nm. The color (FIG. 5) can be measured along the yellow axis at about 10%.

Figure 7:
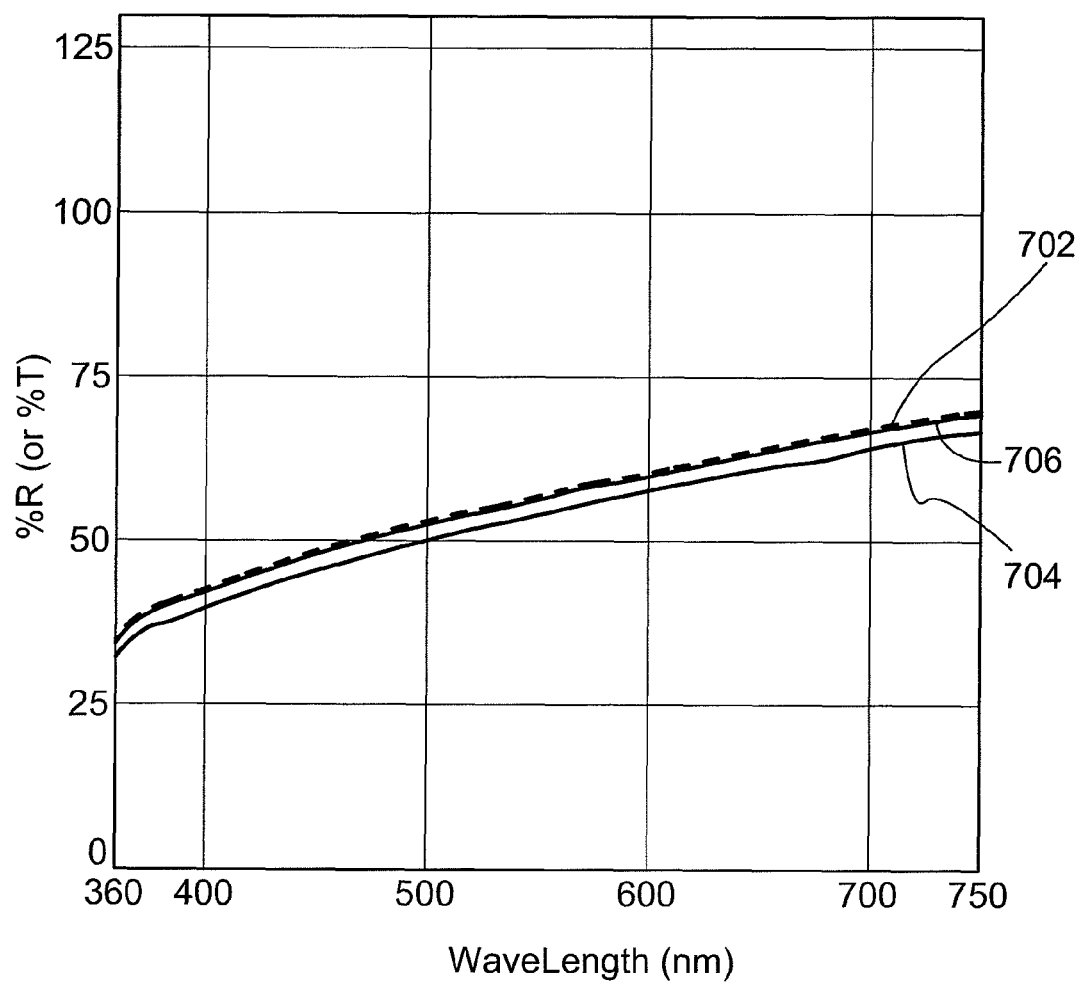
FIG. 7 is an exemplary graphical illustration of the reflectivity for a first, second and third sample towel as a function of wavelength.
Figure 8:
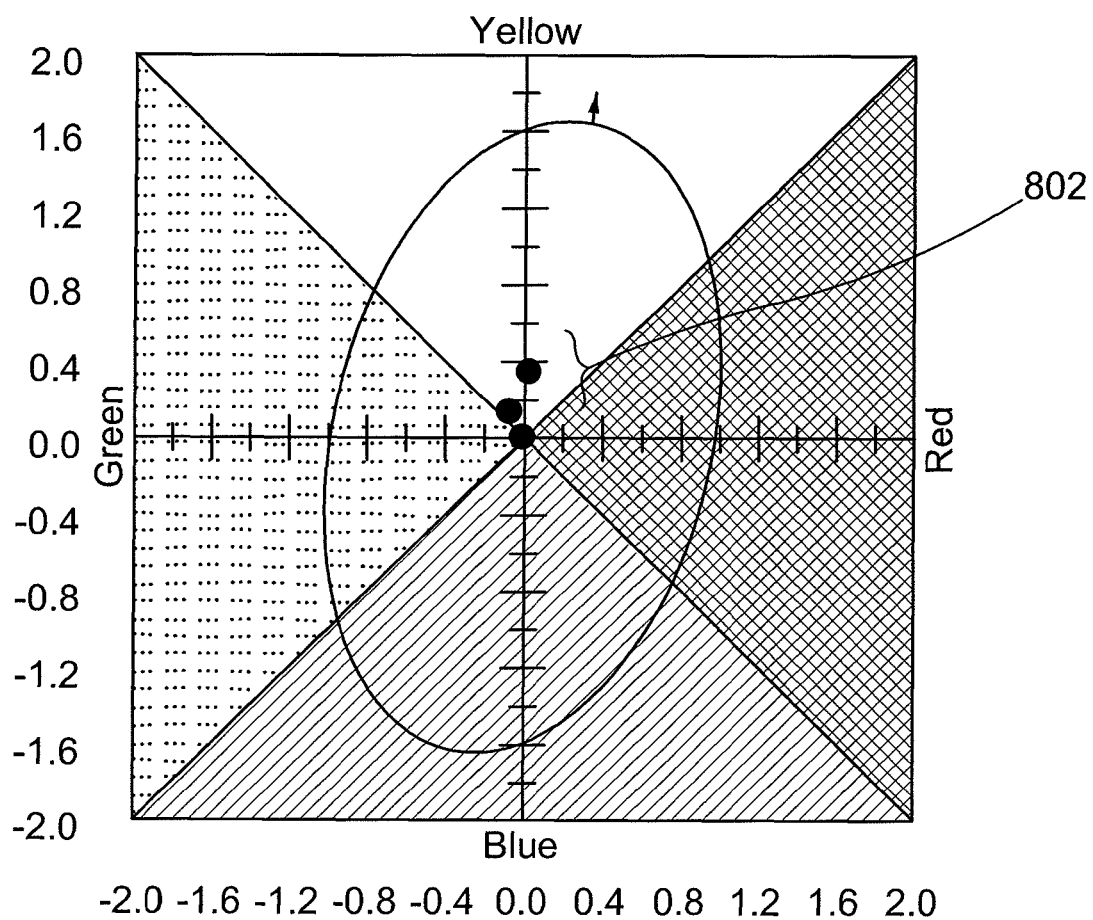
FIG. 8 is a color chart for the first, second and third samples.

In another example, three sample towels, made with the three phase process described in relation to FIG. 2, were measured for their whiteness index, percent reflectance and color percentage. FIGS. 6-8 show the measurement results FIG. 6 illustrates the whiteness of three samples, whiteness measurements in WI-CIE and in WI-Berg. FIG. 7 illustrates the percent reflectance as a function of the wavelength of light for the three samples. FIG. 8 illustrates the color percentage for the three samples.

In this embodiment, the whiteness 602 of sample 1 can be about 12.22 WI-CIE and the percent reflectance (FIG. 7) can be less than about 50 percent at 400 nm and less than or equal to about 70 Percent at 700 nm. The color (FIG. 8) can be measured along the yellow axis 802 at less than about 0.4.

The whiteness 604 of sample 2 can be about 7.23 WI-CIE and the percent reflectance (FIG. 7) can be less than about 50 percent at 400 nm and less than or equal to about 70 Percent at 700 nm. The color (FIG. 8) can be measured along the yellow axis 802 at less than about 0.4.

The whiteness 606 of sample 3 can be about 10.94 WI-CIE and the percent reflectance (FIG. 7) can be less than about 50 percent at 400 nm and less than or equal to about 70 Percent at 700 nm. The color (FIG. 8) can be measured along the yellow axis 802 at less than about 0.4.

In all samples of this embodiment, the percent reflectance can be greater than about 25% at all wavelengths between 360 nm and 750 nm.

While various embodiments have been described above, it should be understood that they have been presented by way of example only, and not limitation. Where methods described above indicate certain events occurring in certain order, the ordering of certain events can be modified. Additionally, certain of the events can be performed concurrently in a parallel process when possible, as well as performed sequentially as described above. Although various embodiments have been described as having particular features and/or combinations of components, other embodiments are possible having a combination of any features and/or components from any of embodiments where appropriate. Furthermore, while certain temperatures, pressures, and other measurements, calculations, and/or other values are described in approximate terms, the values used are not meant to be exact and a range of values can be used, for example plus or minus 10 percent. By way of example, while a temperature may be described as 120 degrees Celsius, the temperature can be between about 108 degrees Celsius and about 132 degrees Celsius, preferably between about 114 degrees Celsius and about 126 degrees Celsius, and most preferably about 120 degrees Celsius.

While the present disclosure and what the best modes of the inventions have been described in a manner establishing possession hereof by the inventors and enabling those of ordinary skill in the art to make and use the same, it will be understood and appreciated that there are many equivalents to the exemplary embodiments disclosed herein and that modifications and variations may be made thereto without departing from the scope and spirit of the inventions, which are to be limited not by the exemplary embodiments but by the appended claims.

What is claimed:

1. A dye free medical towel, comprising:
a cotton absorbent cloth having:
a reflectance percentage value of greater than about 25 and less than about 75, between about 360 nm and about 750 nm,
a whiteness value of less than about 50% WI-CIE,
an absorbency rate of greater than about 2 millimeters per second; and
a lint release less than 700,000 particles of 0.5 micron size or greater.

2. The dye free medical towel of claim 1, wherein the color of the cotton absorbent cloth is substantially pantone 400.

3. The dye free medical towel of claim 1, wherein the cotton absorbent cloth has a reflectance percentage value of greater than about 25 and less than about 70, between about 400 nm and about 700 nm.

4. The dye free medical towel of claim 1, wherein cotton absorbent cloth has a weight of water per weight of fabric ratio of greater than about 3 as measured by ASTM 4772.

5. The dye free medical towel of claim 1, wherein the absorbency rate is greater than about 3 millimeters per second.

6. The dye free medical towel of claim 1, wherein the whiteness value is less than about 35% WI-CIE.

7. A dye free medical towel, comprising:
a non-irritant woven cotton absorbent cloth having:
- a reflectance percentage value of greater than about 50 and less than about 70, between about 400 nm and about 700 nm,
- a whiteness value of less than about 25% WI-CIE,
- an absorbency rate of greater than about 2 millimeters per second; and
- a lint release less than about 100,000 particles of 0.3 micron size or greater.

8. The dye free medical towel of claim 7, wherein the absorbency rate is greater than about 3 millimeters per second.

9. The dye free medical towel of claim 7, wherein non-irritant woven absorbent cloth has a lint release of less than about 70,000 particles of 0.5 micron size or greater.

10. The dye free medical towel of claim 7, wherein the non-irritant woven absorbent cloth includes a color value of less than about 0.4 measured in the yellow spectrum.

11. The dye free medical towel of claim 7, wherein non-irritant woven cotton absorbent cloth has a weight of water per weight of fabric ratio of greater than about 3 as measured by ASTM 4772.

* * * * *